United States Patent [19]

Asakawa et al.

[11] 4,064,231

[45] Dec. 20, 1977

[54] DENTIFRICE COMPOSITION

[75] Inventors: Toshiro Asakawa, Funabashi; Atsuo Ishida, Chiba; Shizuo Hayashi, Sugitomachi, all of Japan

[73] Assignee: Kao Soap Co., Ltd., Tokyo, Japan

[21] Appl. No.: 715,378

[22] Filed: Aug. 18, 1976

[30] Foreign Application Priority Data

Sept. 4, 1975 Japan ............................ 50-107421

[51] Int. Cl.$^2$ ........................................... A61K 7/18
[52] U.S. Cl. .................................................. 424/52
[58] Field of Search ................................... 424/49–58

[56] References Cited

U.S. PATENT DOCUMENTS 3,855,147 12/1974 Granquist ........................... 252/317

Primary Examiner—Shep K. Rose
Attorney, Agent, or Firm—Blanchard, Flynn, Thiel, Boutell & Tanis

[57] ABSTRACT

A dentifrice composition comprising a water-soluble fluoride of the type customarily added to dentifrices as a caries-preventing agent, in an amount of 100 to 2,000 ppm calculated as fluorine, and 0.3 to 13% by weight of montmorillonite having the following composition (% by weight, calculated on an anhydrous basis):

$SiO_2$ : 60.0 – 70.0
$MgO$ : 2.0 – 5.0
$Fe_2O_3$ : 0 – 2.0
$Al_2O_3$ : 20.0 – 30.0
$Na_2O$ : 2.0 – 5.0 or hectorite having the following composition (% by weight, calculated on an anhydrous basis):

$SiO_2$ : 50.0 – 65.0
$Na_2O$ : 2.5 – 5.0
$Fe_2O_3$ : 0 – 2.0
$MgO$ : 20.0 – 30.0
$Li_2O$ : 0.6 – 2.0

3 Claims, No Drawings

DENTIFRICE COMPOSITION

BACKGROUND OF THE INVENTION

1. Field of the Invention

The present invention relates to a dentifrice composition which has a caries-preventing effect that is maintained for a long time. More particularly, the invention relates to a fluorine-containing dentifrice composition in which the reduction of the content of water-soluble fluoride material with the passage of time is prevented by incorporating montmorillonite or hectorite having a specific composition, into the dentifrice composition.

2. Description of the Priot Art

Fluorine is now considered to be the most effective of the currently available caries-preventing agents. Sodium fluoride, sodium monofluorophosphate, stannous fluoride and the like are conventionally incorporated into dentifrices for this purpose. It is generally considered that fluorine ions react with hydroxyapatite in the tooth enamel to form fluoroapatite, whereby the dentin is hardened, the acid resistance of the dentin is enhanced and the resistance of the dentin against attacks of bacteria and acids is increased. According to another theory, it is said that fluorine ions prevent bacteria from adhering to the tooth surfaces. Although a definitive theory has not been established as regards the caries-preventing effect of fluorine ions, by various clinical tests it has been confirmed that fluorine ions have an excellent caries-preventing effect.

A polishing agent such as calcium phosphate dibasic anhydride ($CaHPO_4$), its dihydrate ($CaHPO_4.2H_2O$), calcium carbonate, calcium pyrophospate and/or other calcium salts are incorporated in dentifrices in an amount of about 50 vol. % of the total dentifrice. Calcium ions become dissolved in a dentifrice in a minute amount and gradually react with fluorine ions to form water-insoluble calcium fluoride which has no caries-preventing effect. Accordingly, the caries-preventing effect of a fluorine ion-containing dentifrice is gradually reduced with the passage of time.

SUMMARY OF THE INVENTION

We have discovered that if montmorillonite or hectorite having a specific composition is incorporate into a dentifrice, the reduction of the water-soluble fluoride concentration in the dentifrice with the passage of time can be effectively reduced. We have now completed the present invention based on this finding.

More specifically, in accordance with the present invention, there is provided a dentifrice composition comprising (A) a conventional water-soluble fluoride of the type customarily added to a dentifrice as a caries-preventing agent, present in an amount of 100 to 2,000 ppm calculated as fluorine, and (B) 0.3 to 13% by weight of montmorillonite having the following composition (% by weight, calculated on an anhydrous basis):

$SiO_2$ : 60.0 - 70.0
$MgO$ : 2.0 - 5.0
$Fe_2O_3$ : 0 - 2.0
$Al_2O_3$ : 20.0 - 30.0
$Na_2O$ : 2.0 - 5.0 or hectorite having the following composition (% by weight, calculated on an anhydrous basis):

$SiO_2$ : 50.0 - 65.0
$Na_2O$ : 2.5 - 5.0  $Fe_2O_3$ : 0 - 2.0  $MgO$ : 20.0 - 30.0
$Li_2O$ : 0.6 - 2.0

The foregoing proportions of the above-listed ingredients of montmorillonite and hectorite are critical. The montomorillonite and hectorite can also contain additional components which do not alter the properties thereof for the purposes of the invention. For example, montomorillonite commonly contains from zero to about 6 wt.% of $CaO$ and $K_2O$ and the presence of same does not alter the results. Likewise, hectorite can contain zero to about 5 wt.% of $Al_2O_3$ and from zero to about 13 wt. % of $CaO$ plus $K_2O$ and the presence of same does not alter the results. These additional components are in the nature of inert substances that do not appreciably change the results.

Any of the fluorides that are customarily incorporated in dentifrices as a caries-preventing agent, such as sodium fluoride, potassium fluoride, lithium fluoride, ammonium fluoride, sodium monofluorophosphate, stannous fluoride and manganese fluoride, can be employed in the present invention. If the amount of the fluoride is too small, the intended caries-preventing effect cannot be attained, and if the amount of the fluoride is too large, adverse effects are brought about. Accordingly, the fluoride is added in an amount of 100 to 2,000 ppm, preferably 300 to 1,200 ppm, calculated as fluorine.

The effects of montmorillonite or hectorite having the above-stated specific compositions were found and confirmed by the following experiment:

Dentifrice samples were prepared containing montmorillonite or hectorite having certain compositions, as set forth in Table 2, and the other dentifrice components as listed in Table 1. For each sample, the water-soluble fluoride ion concentration was measured just after preparation of the dentifrice, after 3 months' storage at room temperature and after 3 months' storge at 40° C.

The compositions of the montomorillonites and hectorites tested are listed in Table 2. The montomorillonite or hectorite was added in an amount of 5% by weight. The results (ratio of reduction of water-soluble fluoride with passage of time) of the water-soluble fluoride ion concentrations are listed in Table 3.

Table 1

| Composition (% by weight) of Dentifrice Sample | |
| --- | --- |
| Component | Content |
| Calcium phosphate, dibasic dihydrate | 45 |
| Sorbitol | 20 |
| Sodium lauryl sulfate | 1.8 |
| Propylene glycol | 3.5 |
| Sodium monofluorophosphate | 0.7 |
| Montmorillonite or hectorite | 5.0 |
| Sodium carboxymethylcellulose, perfume, preservative, Saccharin | minor amounts |
| Water | balance |
| Total | 100 |

Table 2

| Composition (% by weight, calculated on an anhydrous basis) of Montmorillonite and Hectorite Tested | | | | | | | | | |
| --- | --- | --- | --- | --- | --- | --- | --- | --- | --- |
| | Montmorillonite | | | | | Hectorite | | | |
| | A* | B** | C** | D** | E** | F* | G** | H** | I** |
| $SiO_2$ | 64.7 | 61.3 | 69.7 | 51.1 | 84.2 | 59.3 | 56.2 | 44.3 | 76.7 |
| $Al_2O_3$ | 25.0 | 24.5 | 16.7 | 31.9 | 5.4 | 1.4 | 3.4 | 1.0 | 0.9 |

Table 2-continued

| | Composition (% by weight, calculated on an anhydrous basis) of Montmorillonite and Hectorite Tested | | | | | | | | |
|---|---|---|---|---|---|---|---|---|---|
| | Montmorillonite | | | | | Hectorite | | | |
| | A* | B** | C** | D** | E** | F* | G** | H** | I** |
| MgO | 3.9 | 1.5 | 2.1 | 6.4 | 0.9 | 26.2 | 23.2 | 34.2 | 5.4 |
| $Na_2O$ | 3.3 | 1.4 | 2.1 | 5.3 | 1.2 | 3.5 | 0.8 | 1.0 | 0.9 |
| $Fe_2O_3$ | 1.8 | 4.3 | 3.9 | 3.2 | 4.4 | 0.5 | 3.3 | 5.6 | 3.2 |
| CaO | 0.8 | 3.9 | 3.9 | 1.2 | 3.1 | 7.8 | 10.1 | 12.2 | 11.0 |
| $K_2O$ | 0.1 | 2.8 | 1.1 | 0.9 | 0.7 | 0.1 | 2.5 | 1.0 | 1.6 |
| $Li_2O$ | 0.0 | 0.0 | 0.0 | 0.0 | 0.0 | 1.3 | 0.4 | 0.2 | 0.3 |

*: sample of the present invention
**: comparative sample

Table 3

Water-Soluble Fluoride ion Concentration[1] and Ratio of Reduction Thereof with Passage of Time[2]

| Sample | Concentration (ppm) Just After Preparation | After 3 Months' Storage at Room Temperature | | After 3 Months' Storage at 40° C | |
|---|---|---|---|---|---|
| | | Concentration (ppm) | Reduction Ratio (%) | Concentration (ppm) | Reduction Ratio (%) |
| A (present invention) | 910 | 880 | 3 | 810 | 11 |
| B (comparison) | 920 | 820 | 11 | 700 | 24 |
| C (comparison) | 920 | 810 | 12 | 690 | 25 |
| D (comparison) | 920 | 770 | 16 | 610 | 34 |
| E (comparison) | 910 | 760 | 16 | 590 | 35 |
| F (present invention) | 920 | 850 | 8 | 760 | 17 |
| G (comparison) | 910 | 810 | 11 | 690 | 24 |
| H (comparison) | 920 | 760 | 17 | 600 | 35 |
| I (comparison) | 910 | 750 | 18 | 610 | 33 |
| control | 900 | 760 | 16 | 600 | 33 |

Notes:

1. Method for Determination of Water-soluble Fluoride ion Concentration

To 1 g of the sample was added 50 cc of pure water, and the mixture was agitated for 30 minutes and subjected to centrifugal separation at 8,000 rpm for 45 minutes. Then, 25 cc of the supernatant liquid was collected. Subsequent operations were conducted according to the fluorine-containing dentifrice test method described in Official Gazette of Drugs, Cosmetics and Medical Instruments, No. 660, pages 263–264.

2. Ratio of Reduction with Passage of Time

The ratio of the reduction of the water-soluble fluoride ion concentration with the passage of time was calculated according to the following formula:

$$R (\%) = [(A - B) / A] \times 100$$

in which R is the ratio of the reduction of the water-soluble fluoride ion concentration with the passage of time, A stands for the water-soluble fluoride ion concentration just after preparation of the dentifrice composition, and B stands for the effective fluorine concentration after storage.

From the results shown in Tables 2 and 3, it will be understood that montmorillonite A and hectorite F both have a very high effect of minimizing the reduction of the water-soluble fluoride concentration of the dentifrice.

When montmorillonite A is compared with the other montmorillonites B, C, D and E, it will be apparent that montmorillonite composition A has an unexpectedly better effect of minimizing the reduction of the water-soluble fluoride concentration. Namely, montmorillonite having a composition (% by weight, calculated on an anhydrous basis) of 60.0 – 70.0 of $SiO_2$, 20.0 – 30.0 of $Al_2O_3$, 2.5 – 5.0 of MgO, 2.0 – 5.0 $Na_2O$ and 0 – 2.0 of $Fe_2O_3$ is very effective. Since a calcium salt such as calcium phosphate, dibasic dihydrate, is contained in a large amount in the dentifrice, the CaO content of the montmorillonite is not particularly significant, but it is preferred that the CaO content be lower than 2.0% by weight.

When hectorite F is compared with the other hectorites G, H and I, is seen that hectorite F is very effective for minimizing the reduction of the water-soluble fluoride concentration, and from the above comparison an effective hectorite composition is apparent. Namely, a hectorite composition (% by weight, calculated on an anhydrous basis) of 50.0 – 65.0 of $SiO_2$, 20.0 – 30.0 of MgO, 2.5 – 5.0 of $Na_2O$, 0.6 – 2.0 of $Li_2O$ and 0 – 2.0 of $Fe_2O_3$ is very effective. The CaO content in the hectorite is not particularly significant, but it is preferred that the CaO content of the hectorite be lower than 10.0% by weight.

The process for preparing the montmorillonite or hectorite having a specific composition is not particularly critical. It is, however, preferred to use a powdery product obtained by collecting a starting ore of a high quality having low contents of impurities, such as chrystoperlite, feldspar, mica and quartz, from a bentonite layer, removing the impurities by water sieving, and drying and pulverizing the sieved product.

These montmorillonites and hectorites have a high base exchange capacity and hence, they posses excellant water-absorbing, swelling and thickening properties. Further, since they are negatively charged, they have a high activity of adsorbing cations such as $Ca^{++}$.

When too small an amount of the montmorillonite or hectorite having the specific compositions described above, is incorporated in a dentifrice, the intended effect of minimizing the reduction of the water-soluble fluoride concentration cannot be attained. When the amount of the montmorillonite or hectorite is too large, the cream is too hard and a pasty product is obtained. Accordingly, the montomorillonite or hectorite is incorporated in an amount of 0.3 to 13% by weight, preferably 1 to 6% by weight.

The dentifrice composition of the present invention also contains, as a base, a mixture of a polishing agent, a swelling agent and a foaming agent, as is conventional.

The polishing used as a base of the dentifrice can be any conventional polishing agent, or mixtures thereof, such as calcium phosphate dibasic anhydride, the dihydrate thereof, calcium carbonate, water-insoluble alkali metal metaphosphates, calcium pyrophosphate, aluminum hydroxide, silica, kaolin and alumina. The amount of the polishing agent in the dentifrice composition if 5 to 70% by weight, preferably 15 to 60%, based on the total weight of the dentifrice composition.

The swelling agent employed a base of the dentifrice can be any conventional agent such as glycerin, sorbitol, propylene glycol or sodium polycarboxylate. It can be employed in an amount of 5 to 40% by weight, preferably 10 to 30% by weight, based on the total weight of the dentifrice composition.

The foaming agent, i.e. organic surfactant, can be selected from conventional dentifrice foaming agents, such as sodium alkyl sulfate ($C_8$–$C_{20}$), sodium N-lauroyl sarcosinate, sodium monoglyceride sulfate, sucrose ester, sodium alkylsulfoacetate, sodium sulfocolaurate or alkanesulfonate. It can be employed in an amount of 0.3 to 5.0% by weight, based on the total weight of the dentifrice composition.

The dentifrice composition of the present invention can obtain other known additives in addition to the base, the water-soluble fluoride and the special monomorillonite or hectorite. For example, it is possible to incorporate 0.3 to 5.0% by weight of a binder such as sodium carboxymethyl cellulose, hydroxyethyl cellulose, sodium carboxymethyl hydroxyethyl cellulose, methyl cellulose, carrageen, sodium alginate, xanthan gum, hypnea, guar gum, locust bean gum, gum tragacanth or polyvinyl alcohol, 0.01 to 10.0% by weight of a sweetening agent such as saccharin sodium and 0.01 to 1.0% by weight of a preservative such as sodium benzoate or ethyl p-hydroxybenzoate. Still in addition, various pharmaceutical agents and perfumes can be added according to need. The balance of the dentifrice composition consists essentially of water.

When the montomorillonite or hectorite having the above-mentioned specific composition is used for preparation of a dentifrice composition, water is added to the powdery montomorillonite or hectorite and the mixture is agitated at at least 100 rpm to disperse the powder in water and to swell the powder with water. It is not especially necessary to elevate the agitation temperature, but if the agitation is conducted at about 50° to about 60° C, the viscosity is increased in a short time. It is also possible to disperse powdery montomorillonite or hectorite into an aqueous solution of sorbitol or glycerin containing saccharin sodium, a preservative and other additives homogeneously dissolved therein and agitate the dispersion at at least 100 rpm to effect swelling of the powder. A dentifrice can be prepared by adding a base, a pharmaceutical agent and the like to the above dispersion, agitating the mixture, adding the foaming agent and a perfume to the mixture, and defoaming and agitating the resulting composition.

The present invention will now be described in detail by reference to the following Examples, in which all references to "parts" mean parts by weight.

EXAMPLE 1

| | |
|---|---|
| Glycerin | 14 parts |
| Sorbitol | 12 parts |
| Sodium carboxymethylcellulose | 0.5 part |
| Calcium phosphate, dibasic dihydrate | 40 parts |
| Sodium lauryl sulfate | 1.6 parts |
| Sodium benzoate | 0.2 part |
| Montmorillonite A shown in Table 2 | 2.5 parts |
| Sodium monofluorophosphate | 0.7 part |
| Flavoring component and perfume | conventional amounts |
| Water | balance |
| Total | 100 parts |

Sodium carboxymethylcellulose was dispersed in glycerin, and sorbitol and water were added to the dispersion and the mixture was agitated until a homogeneous transparent viscous solution was obtained. Then, sodium benzoate, the flavoring component and montomorillonite were dissolved in the solution, and calcium phosphate, dibasic dihydrate, and sodium monofluorophosphate were added and the mixture was sufficiently kneaded to obtain a homogeneous paste. Finally, sodium lauryl sulfate and the perfume were added to the paste while the paste was being defoamed. There was obtained a useful dentifrice composition.

EXAMPLE 2

| | |
|---|---|
| Sorbitol | 15 parts |
| Propylene glycol | 0.5 part |
| Methyl p-hydroxybenzoate | 0.2 part |
| Sodium lauryl sulfate | 1.7 parts |
| Calcium carbonate | 43 parts |
| Montmorillonite A shown in Table 2 | 4.0 parts |
| Sodium monofluorophosphate | 0.7 part |
| Flavoring component and perfume | conventional amounts |
| Water | balance |
| Total | 100 parts |

Methyl p-hydroxybenzoate and the flavoring component were added to sorbitol and water, and montmorillonite was added to the solution and the mixture was agitated until a homogeneous viscous solution was obtained. Then, calcium carbonate and sodium monofluorophosphate were added to the solution and the mixture was sufficiently kneaded to obtain a homogeneous paste. Finally, sodium lauryl sulfate and the perfume were added while the paste was being defoamed.

EXAMPLE 3

| | |
|---|---|
| Glycerin | 20 parts |
| Sodium carboxymethylcellulose | 0.3 part |
| Calcium phosphate, dibasic dihydrate | 0.1 part |
| Sodium benzoate | 0.1 part |
| Hectorite F shown in Table 2 | 5.0 parts |
| Sodium lauryl sulfate | 1.9 parts |
| Sodium monofluorophosphate | 0.7 part |
| Flavoring component and perfume | conventional amounts |
| Water | balance |
| Total | 100 parts |

A dentifrice was prepared from the above components in the same manner as in Example 1.

EXAMPLE 4

| | |
|---|---|
| Glycerin | 18 parts |
| Sodium carboxymethylcellulose | 1.0 part |
| Calcium phosphate, dibasic dihydrate | 42 parts |
| Sodium benzoate | 0.1 part |
| Montmorillonite A shown in Table 2 | 6.0 parts |
| Sodium monofluorophosphate | 0.7 part |

| -continued | |
|---|---|
| Flavoring component and perfume | conventional amounts |
| Water | balance |
| Total | 100 parts |

A dentifrice was prepared from the above components in the same manner as in Example 1.

The embodiments of the invention in which an exclusive property or privilege is claimed are defined as follows:

1. A dentifrice composition containing a water-soluble fluorine-containing caries-preventing agent in an amount of from 100 to 2,000 ppm calculated as fluorine, and from 0.3 to 13 percent by weight of montmorillonite having the composition, in terms of percent by weight, calculated on an anhydrous basis,

| | |
|---|---|
| $SiO_2$ | 60.0 to 70.0 |
| $MgO$ | 2.0 to 5.0 |
| $Fe_2O_3$ | zero to 2.0 |
| $Al_2O_3$ | 20.0 to 30.0 |
| $Na_2O$ | 2.0 to 5.0 |

2. A dentifrice as claimed in claim 1 containing from 300 to 1,200 ppm, calculated as fluorine, or said caries-preventing agent, and from 1 to 6% by weight of said substance.

3. A dentifrice composition as claimed in claim 1 in which the balance of said composition consists essentially of from 5 to 70wt. % of a polishing agent, from 5 to 40 wt. % of a swelling agent, from 0.5 to 5 wt. % of a foaming agent and water.

* * * * *

UNITED STATES PATENT AND TRADEMARK OFFICE
CERTIFICATE OF CORRECTION

PATENT NO. : 4 064 231

DATED : December 20, 1977

INVENTOR(S) : Toshiro Asakawa, Atsuo Ishida and Shizuo Hayashi

It is certified that error appears in the above-identified patent and that said Letters Patent are hereby corrected as shown below:

Column 8, line 12; change "or" to ---of---.

Column 8, line 14; change "substance" to ---montmorillonite---.

Signed and Sealed this

Twenty-eighth Day of March 1978

[SEAL]

Attest:

RUTH C. MASON
*Attesting Officer*

LUTRELLE F. PARKER
*Acting Commissioner of Patents and Trademarks*